United States Patent
Wu et al.

(10) Patent No.: US 10,130,421 B2
(45) Date of Patent: Nov. 20, 2018

(54) METHOD OF MANUFACTURING A MAGNETIC GUIDED CATHETER

(71) Applicant: ST. JUDE MEDICAL, ATRIAL FIBRILLATION DIVISION, INC., St. Paul, MN (US)

(72) Inventors: Kirk Kochin Wu, Walnut, CA (US); Yongxing Zhang, Irvine, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 281 days.

(21) Appl. No.: 14/993,616

(22) Filed: Jan. 12, 2016

(65) Prior Publication Data

US 2016/0199128 A1     Jul. 14, 2016

Related U.S. Application Data

(62) Division of application No. 12/167,417, filed on Jul. 3, 2008, now abandoned.

(51) Int. Cl.
| | |
|---|---|
| *H01R 43/00* | (2006.01) |
| *A61B 18/14* | (2006.01) |
| *A61M 25/00* | (2006.01) |
| *A61M 25/01* | (2006.01) |
| *A61B 17/00* | (2006.01) |
| *A61B 18/00* | (2006.01) |

(52) U.S. Cl.
CPC ..... *A61B 18/1492* (2013.01); *A61M 25/0009* (2013.01); *A61M 25/0127* (2013.01); *A61B 2017/00526* (2013.01); *A61B 2018/00357* (2013.01); *A61B 2018/00577* (2013.01); *Y10T 29/49174* (2015.01)

(58) Field of Classification Search
CPC ...... A61B 18/1492; A61B 2017/00526; A61B 2018/00577; A61B 2018/00357; A61M 25/0009; A61M 25/0127; Y10T 29/49117; Y10T 29/49174; Y10T 29/49181; Y10T 29/49208
USPC .................. 29/825, 857, 861, 876; 128/899; 439/589

See application file for complete search history.

(56) References Cited

U.S. PATENT DOCUMENTS

| | | | |
|---|---|---|---|
| 3,514,081 A | | 5/1970 | Cavanaugh et al. |
| 4,713,021 A | * | 12/1987 | Kobler ............... H01R 13/5205 439/589 |
| 5,911,720 A | | 6/1999 | Bourne et al. |
| 6,173,199 B1 | * | 1/2001 | Gabriel .................. A61J 15/00 128/899 |
| 6,385,472 B1 | | 5/2002 | Hall et al. |
| 6,817,364 B2 | | 11/2004 | Garibaldi et al. |
| 6,980,843 B2 | | 12/2005 | Eng et al. |
| 2002/0058866 A1 | | 5/2002 | Segner et al. |
| 2004/0158142 A1 | | 8/2004 | Hall et al. |
| 2007/0016131 A1 | | 1/2007 | Munger et al. |

(Continued)

*Primary Examiner* — Donghai D Nguyen
(74) *Attorney, Agent, or Firm* — Dykema Gossett PLLC

(57) ABSTRACT

Magnetic guided ablation catheters and methods of manufacture are disclosed. In an exemplary embodiment, a catheter includes a unitary flexible tubing having a proximal end and a distal end. A plurality of magnets are positioned along an axis of the unitary flexible tubing, the plurality of magnets provided within the unitary flexible tubing. During operation, the plurality of magnets are responsive to an external magnetic field to selectively position and guide the catheter within a body of a patient.

15 Claims, 5 Drawing Sheets

(56) References Cited

U.S. PATENT DOCUMENTS

2007/0049846 A1 3/2007 Brown et al.
2010/0004632 A1 1/2010 Wu et al.

* cited by examiner

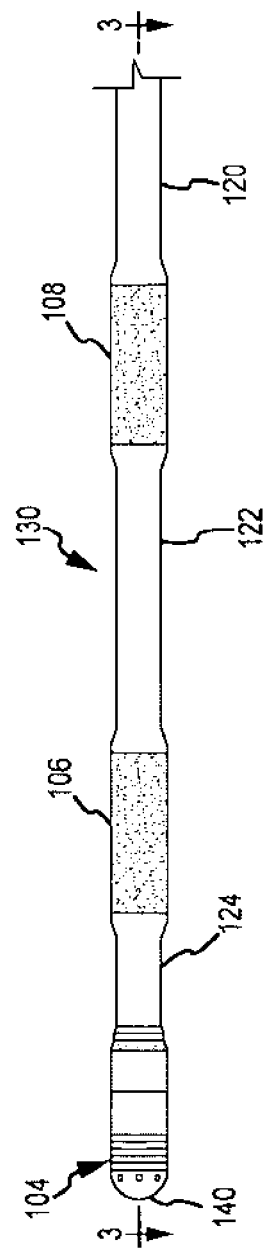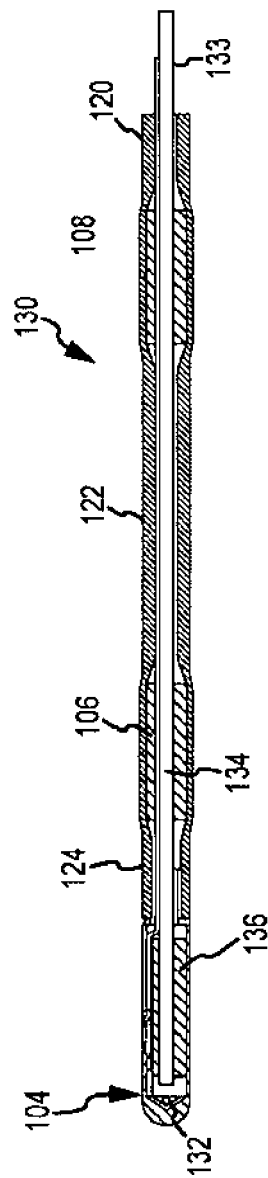

METHOD OF MANUFACTURING A MAGNETIC GUIDED CATHETER

This application is a divisional of U.S. application Ser. No. 12/167,417, filed 3Jul. 2008, now pending (the '417 application). The '417 application is hereby incorporated by reference as though fully set forth herein.

BACKGROUND OF THE INVENTION a. Field of the Invention

This invention relates generally to manufacturing of medical instruments, and, more specifically, to the manufacture of a navigable ablation catheter device positionable within a body of a patient using an externally applied magnetic field.

b. Background Art

Catheters are flexible, tubular devices that are widely used by physicians performing medical procedures to gain access into interior regions of the body. Careful and precise positioning of the catheters within the body is important to successfully completing such medical procedures. This is particularly so when catheters are used to produce emissions of energy within the body during tissue ablation procedures. Conventionally, positioning of such catheters was accomplished with mechanically steerable devices. More recently, magnetically navigable catheter devices have been developed that may be navigated with an externally applied magnetic field. Such catheter devices can be complex in their construction; and therefore are difficult to manufacture and relatively expensive to produce.

Magnetic stereotactic systems have been developed that are particularly advantageous for positioning of catheters, as well as other devices, into areas of the body that were previously inaccessible. Such systems utilize computer controlled superconducting coils to generate specific magnetic fields or gradients to move a catheter that is provided with magnetic components responsive to such magnetic fields. The magnetic fields and gradients are generated to precisely control the position of the catheter within the patient's body. Once correctly positioned, physicians may operate the catheter, for example, to ablate tissue to clear a passage in the body. Specifically, such stereotactic systems monitor the position of a tip of the catheter in response to the applied magnetic fields of the superconducting coils. The catheter tip may be guided to and positioned in a desired location within the patient's body using well established feedback and control algorithms.

Manufacture of magnetic-guided catheters can be challenging and time consuming because the catheter shaft has to be fused together to accommodate the magnets. The fusion process must be precisely controlled, including parameters such as temperature, time, side load, and tubing selection, in order to ensure mechanical strength and cosmetic appearance. Therefore, improvements in the manufacture of catheters utilized with magnetic guidance and control systems, such as stereotactic systems, are desired. Specifically, a low cost, yet high performance magnetically guided ablation catheter is desirable which can be manufactured without having to fuse the shaft.

BRIEF SUMMARY OF THE INVENTION

In various embodiments, magnetic guided catheters are disclosed that are manufacturable at relatively low cost while providing high performance for use with, for example, magnetic stereotactic systems.

In one embodiment, the catheter may comprise: a unitary flexible tubing having a proximal end and a distal end; and a plurality of magnets positioned along an axis of the unitary flexible tubing, the plurality of magnets provided within the unitary flexible tubing. The plurality of magnets are responsive to an external magnetic field to selectively position and guide the catheter within a body of a patient.

In another embodiment, the catheter may comprise: a variably-flexible tubing having a proximal end and a distal end, the variably-flexible tubing prefabricated to be unitary in construction; and at least one magnet separately provided from an electrode assembly and spaced from the electrode assembly along an axis of the flexible tubing. The at least one magnet is responsive to an external magnetic field to selectively position and guide the electrode assembly within a body of a patient.

In yet another embodiment, a catheter may comprise: a unitary flexible tubing having a proximal end and a distal end defining substantially an entire length of the catheter; and at least one magnet positioned along an axis of the unitary flexible tubing, the at least one magnet provided within the unitary flexible tubing. The at least one magnet is responsive to an external magnetic field to selectively position and guide the catheter within a body of a patient.

Optionally, the magnet is pushed into the unitary flexible tubing. For example, the magnet may be positioned on a mandrel and pushed into the unitary flexible tubing using a lubricant such as, alcohol, to facilitate receiving at least one magnet therein. Alternatively, the unitary flexible tubing is heat-shrunk over the at least one magnet. There may exist an interference fit between the at least one magnet and the unitary flexible tubing. The interference fit may be formed by an outer diameter of the at least one magnet being larger than an inner diameter of the unitary flexible tubing. For example, the interference fit may be formed by an outer diameter of the at least one magnet being about 0.005 inches larger than an inner diameter of the unitary flexible tubing.

Also optionally, the unitary flexible tubing may have different flexibilities along a length the unitary flexible tubing. In exemplary embodiments, the unitary flexible tubing is more flexible toward the distal end and less flexible toward the proximal end. For example, the unitary flexible tubing may be manufactured with different material properties to provide less flexibility toward the proximal end and more flexibility toward the distal end. Or for example, the unitary flexible tubing may be formed thicker to provide less flexibility toward the proximal end, and the unitary flexible tubing is formed thinner to provide more flexibility toward the distal end. The unitary flexible tubing may include a plurality of segments, each segment having different flexibility. The unitary flexible tubing may include abrupt steps of flexibility between the segments, the abrupt steps defining locations for providing magnets in the unitary flexible tubing.

The catheter may also comprise at least a second magnet, the second magnet spaced from the at least one magnet along the axis of the unitary flexible tubing. The catheter may also comprise at least a third magnet, the third magnet spaced from the second magnet along the axis of the unitary flexible tubing. The second magnet may be spaced from the at least one magnet by a first distance along the axis of the unitary flexible tubing, and the third magnet may be spaced a second distance from the second magnet along the axis of the tubing, wherein the third distance is greater than the second distance. The magnets may have one of a cylindrical shape and an ellipsoidal shape.

The catheter may be configured as at least one of a cardiac ablation catheter, a cardiac electrophysiological mapping catheter, and a cardiac diagnostic pacing stimuli catheter. Accordingly, the catheter may further comprise an electrode assembly at the distal end of the unitary flexible tubing, the electrode assembly comprising a tip electrode and a band electrode. The electrode may be configured as a radiofrequency ablation tip. The electrode assembly may comprise a temperature sensor.

Still other features and method of manufacturing of magnetic guided catheters are disclosed.

BRIEF DESCRIPTION OF THE DRAWINGS

FIG. 2 is a magnified view of a distal end portion of the catheter shown in FIG. 1.

FIG. 3 is a cross sectional view of the distal end portion shown in FIG. 2.

DETAILED DESCRIPTION OF THE INVENTION

Figure 1:
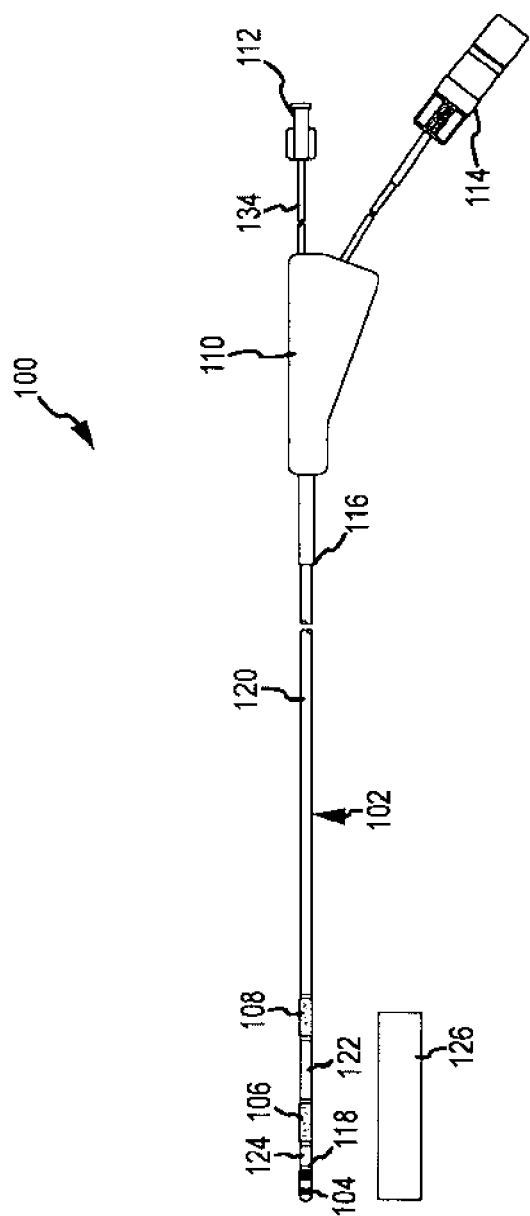
FIG. 1 illustrates a first exemplary magnetic guided catheter.

FIG. 1 illustrates a first exemplary non-steerable, single-use magnetic guided catheter 100 generally including a flexible tubing 102, a tip assembly 104, positioning magnets 106 and 108 separately provided from and spaced from the tip assembly 104, a Y connector 110, a luer device 112, and an electrical connector 114. The electrical connector 114 establishes electrical connection with a power source (not shown) that operates electrodes of the tip assembly 104 to perform, for example, ablation procedures, mapping or pacing procedures, or to perform other aspects of a medical procedure.

Although it will become evident that aspects of the exemplary catheter 100 are applicable to a variety of medical procedures and end uses, the invention will be described principally in the context of a specific example of a magnetic guided catheter. Specifically, the catheter 100 as shown in FIG. 1 is believed to be particularly advantageous as an ablation catheter for creating endocardial lesions during cardiac ablation procedures to treat arrhythmias, and also for cardiac electrophysiological mapping and delivering diagnostic pacing stimuli. However, the invention and the appended claims are not intended to be limited to any specific example, including but not limited to specific examples or embodiments described herein, except when explicitly defined as such in the appended claims.

The Y-connector 110 separates a fluid tube 134 from electrical lead wires extending between the tip assembly 104 and the electrical connector 114. That is, the fluid tube 134 and the lead wires forward of the Y-connector 110 pass internally through the tubing 102, while aft of the NT-connector 110, the fluid tube 134 and the wire leads are exposed and separated for connection to a fluid source (not shown) and a power source, respectively. The electrical connector 114 may be a known connector that may be engaged to a power source or power supply with, for example, plug-in connection. One suitable electrical connector is a 14 pin REDEL® plastic connector commercially available from LEMO of Rohnert Park, Calif., although other connectors from various manufacturers may likewise be utilized.

The luer device 112 in the depicted embodiment, as known in the art, may be used to open or close a flow path so that fluid may be passed through the Y-connector 110 and the tubing 102 to the tip assembly 104 for irrigation purposes. The luer device 112 may be considered optional for certain procedures.

The flexible tubing 102 includes a proximal end 116 coupled to the Y-connector 110, a distal end 118 coupled to the tip assembly 104, and an axial length extending between the proximal and distal ends 116 and 118. In general, the flexible tubing 102 may be fabricated according to known processes, such as extrusion processes. The tubing 102 may be fabricated from any suitable tubing material known in the art of medical instruments, such as engineered nylon resins and plastics, including but not limited to PEBAX® tubing of Ato Fina Chemicals, France.

In an exemplary embodiment, the tubing 102 includes a first portion 120 of the tubing 102 between the Y connector and the magnet 108, a second portion 122 of the tubing 102 between the magnet 106 and 108, and a third portion 124 of the tubing 102 extending between the magnet 106 and the tip assembly 104. In an exemplary embodiment, the first portion 120, the second portion 122 and/or the third portion 124 may be fabricated from different materials, grades of materials, and/or thicknesses of materials for enhanced performance and flexibility of the tubing 102 in use of the catheter assembly 100, as will be explained in more detail below. It is noted, however, that although the tubing 102 may have different portions or "zones", the tubing 102 is manufactured as a unitary piece.

For example, in one embodiment, the first portion 120 of the tubing 102 may include, for example a braided material that is comparatively rigid and kink resistant. The first portion 120 may be formed with different portions of braided material, semi-soft material, and soft material fused to one another so that the first portion 120 becomes increasingly flexible along the axial length as the tube portion 120 approaches the magnet 108. The second portion 122 of the tubing 102 and the third portion 124 may include a soft and flexible material having approximately equal flexible properties. In the illustrated embodiment, each of the tubing portions 120, 122 and 124 between the tip 104 and the magnets 106 and 108 share a common outside diameter of, for example, 7 French, although in other embodiments, the tubing portions 120, 122 and 124 may be another size.

Additionally, and as shown in FIG. 1, the first portion 120 extends for the vast majority of the axial length of the tubing 102 between the proximal and distal ends 116 and 118. The second portion 122 of the tubing 102 extends for a much shorter length than the first portion 120, and the third portion 124 of the tubing extends for a length that is shorter than the second portion 122. By way of example only, in a specific embodiment the first portion 120 extends for an axial length of about 126.3 cm, the second portion 122 extends for an axial length of about 2.2 cm, and the third portion 124 extends for an axial length of about 0.8 cm, although other relative lengths of the tube portions may likewise be employed in other embodiments. The different relative lengths of the tube portions 120, 122 and 124, as well as the different flexible properties of the tube portions 120, 122 and 124, allows the tip assembly 104 to be more precisely positioned within a patient's body, while also avoiding problems of kinks and excessive deflection of the tubing 102 along the majority of its length during use and handling.

As another consequence of the tubing portions 122 and 124 having an unequal length, the magnet 106 is a spaced a first distance from the tip assembly 104, and the magnet 108 is spaced a second and farther distance from the magnet 106 via the tubing portion 122 being longer than the tubing portion 124. Due to the spacing of the magnets 106 and 108 relative to one another and also to the tip assembly 104, which as explained below also includes a positioning magnet, the spacing of the magnets permits adjustment in positioning of the tip assembly 104 in response to variation in an externally applied magnetic field that may otherwise be difficult, if not impossible, if the magnets were provided in an equal or uniform spaced relation to one another. It is contemplated, however, that in another embodiment the tip 104, the magnet 106 and the magnet 108 could be equally spaced from one another if desired.

In operation, the distal end of the catheter 100 including the tip 104 is navigated to the site in the body where a medical procedure, such as an atrial mapping, pacing and ablation are to occur. The distal end may extend, for example, into a heart chamber of a patient. Once the distal end is in the chamber, a magnetic field is applied to provide an orienting force to the distal end, causing the magnets to respond to the applied magnetic field and flex the tubing portions 124 and 122 to precisely position the tip 104 for performance of the procedure at a specific location. The magnetic fields used to orient the tip 104 may be generated with, for example, a magnetic stereotactic system 126. Such stereotactic systems are known and are commercially available from, for example. Stereotaxis of St. Louis, Mo. Such systems may include movable source magnets outside the body of the patient, and operative details of such systems are disclosed in, for example, U.S. Pat. Nos. 6,475,223 and 6,755,816, the disclosures of which are hereby incorporated by reference in their entirety. While the catheter 100 is believed to be particularly advantageous for use with a stereotactic system, it is contemplated that magnetic fields and gradients to deflect the catheter tip 400 may alternatively be generated by other systems and techniques if desired.

FIG. 2 is a magnified view of a distal end portion 130 of the catheter 100 shown in FIG. 1. The tip assembly 104 may be coupled to the tube portion 124 at one end and the magnets 106 and 108 are provided in the tube portion 124.

The tip electrode 140 may be an 8 Fr hemispherical-shaped tip electrode that is, for example, 2 mm in length. The tip electrode 140 is formed with a plurality of open conduits that form the irrigation ports for saline irrigation. The tip electrode 140 may be fabricated from 90% platinum and 10% iridium, or other materials known in the art. The tip electrode 140 may be visually recognizable under fluoroscopic exposure. While formed as an integral unit, the tip electrode 140 may include multiple electrode elements, such as ring electrodes for electrophysiological mapping purposes, spaced from one another by dielectric materials as is known in the art.

The tip assembly 104 is particularly suited for ablation procedures wherein the electrodes 140 are energized to deliver radio frequency waves at the site of an abnormal pathway in the body. Radiofrequency (RF) energy may therefore be coupled to biological tissue surrounding the catheter tip, Ablation procedures are typically used, for example, within the interior chambers of the heart to thermally ablate cardiac tissue. The electrodes 140 may additionally be operated to record intracardiac signals and to provide pacing signals.

FIG. 3 is a cross sectional view of the distal end portion 130 wherein an inner tube 133 defining a central lumen 134 extends through each tube portion 120, 122, and 124, and also through central bores formed in the magnets 105 and 108. The inner tube 133 is smaller in diameter than the tubing 102 and its portions 120, 122 and 124, such that the tube 133 passes through a portion of the internal opening of the tubing 102, while leaving room to spare. Thus, internal areas of the tubing 102 that are not occupied by the lumen may be used to accommodate lead wires for electrical components of the lip assembly 104.

The tip assembly 104 may also include a positioning magnet 136, with the tube 133 and lumen 134 also passing through a central bore in the magnet 136. The lumen 134 is in fluid communication with the luer 112 (FIG. 1) on one end and with the irrigation ports 132 of the tip assembly 104 at the other. Thus, an irrigation fluid, such as saline, may be injected through the distal end portion 130. The tube 133 may be, for example, a braided polyimide tube that maintains the flow path through the lumen 134 in all orientations of the tip assembly 104, without compromising the flexibility of the tubing 102.

The magnets 106 and 108 are each permanent magnets formed from, for example, neodymium-iron boron-45 (Nd-FeB-45) into an elongated cylindrical shape. The magnets 106 and 108 may comprise flexible magnets. The flexible magnets may be slacked, flexible magnetic elements, or made of flexible magnet strips, or extruded flexible magnets in a tubular form. Alternatively, the magnets 106 and 108 may be formed from other materials and may have different shapes.

In an exemplary embodiment, the magnets 106 and 108 are generally cylindrical shaped permanent magnets. A central bore may extend through the magnets 106 and 108 so that tubing and/or wiring can extend through the bore in the magnet and pass centrally through the magnets 106 and 108. Alternatively, or in addition to, the magnets 106 and 108 may be formed with a recess on the outer exterior that allows the lead wires to pass around the outer surface of the magnets 106 and 108.

The magnets 106 and 108 may be installed within tubing 102 in such a manner so that the tubing remains unitary in construction. Accordingly, the catheter can be manufactured without requiring magnet-shaft fusion, and thus there are no joints, ensuring high reliability and safety of the catheter. In comparison with the magnet-shaft fusion assembly procedures noted in the prior art, the unitary tubing is easier to manufacture, takes less time to manufacture, and does not require a fusion machine, which tend to be expensive and may require validation and qualification prior to use. In addition, undesirable stiffness is avoided because the junctions between the magnet and the shaft are eliminated.

Figure 4:
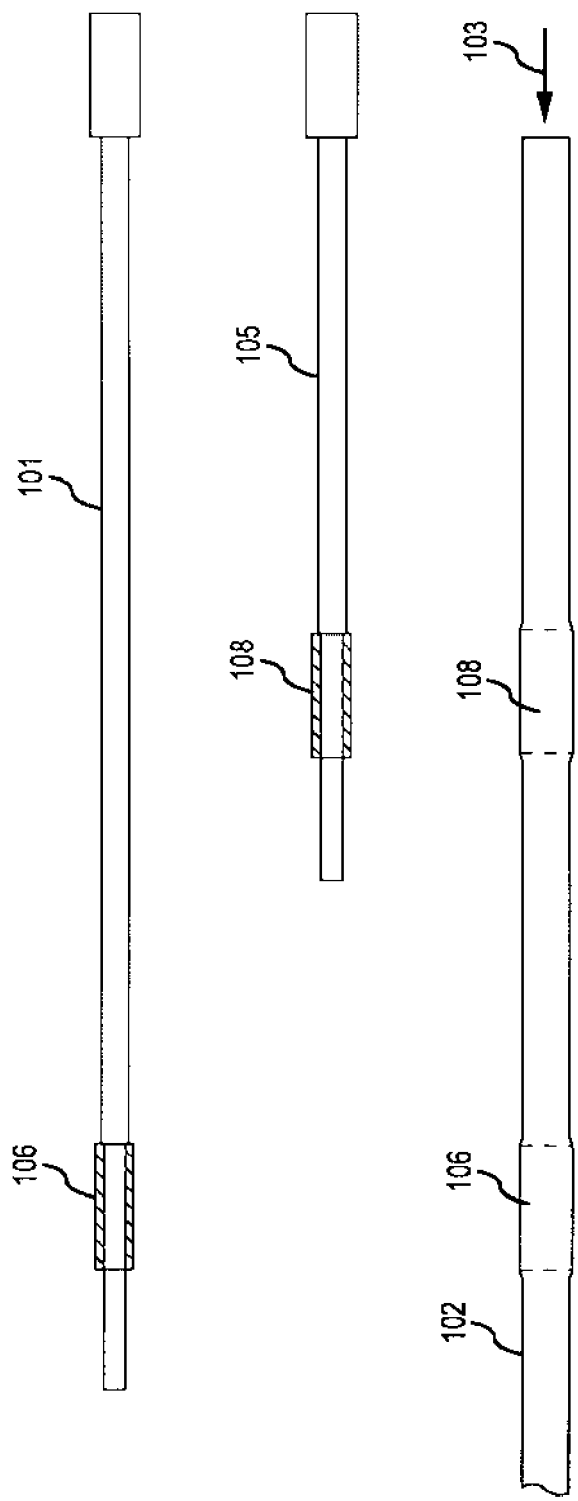
FIG. 4 illustrates an exemplary manufacture process for the magnetic guided catheter.

FIG. 4 illustrates an exemplary manufacture process for the magnetic guided catheter. In an exemplary embodiment, the magnets 106 and 108 may be pushed into the tubing during the manufacture process in the direction illustrated by arrow 103. For example, the magnets 106 and 108 may be positioned on mandrels 101 and 105, respectively, and pushed into the tubing 102 one at a time using a lubricant such as, alcohol, to facilitate receiving the magnets 106 and 108 therein. The alcohol conveniently evaporates after a short time. The magnets 106 and 108 are shown mounted on the mandrels 101 and 105 outside of the tubing 102. The magnets 106 and 108 are inserted into the tubing 102 one at a time, by pushing the mandrels 101 and 105 separately and sequentially in the direction of arrow 103.

According to this method, there may exist an interference fit between the magnets 106 and 108, and the tubing 102, thereby securing the position of the magnets 106 and 108. It is noted that the drawings are exaggerated to better illustrate the interference fit. In reality, the interference fit may not be as pronounced as it is shown in the drawings. The interference fit may be formed by an outer diameter of the at least one magnet being larger than an inner diameter of the unitary flexible tubing. For example, the interference fit may be formed by the magnets 106 and 108 having an outer diameter about 0.005 inches larger than the inner diameter of the tubing 102.

In another exemplary embodiment, the magnets 106 and 108 may be pushed into the tubing 102 without any interference fittings. In this embodiment, the tubing 102 may be wrapped in heat-shrink film or heat-shrink tubing. The heat-shrink process shrinks the heat-shrink film or tubing around the tubing 102 so that the position of magnets 106 and 108 is secured within the tubing 102.

Heat-shrink processes are well understood in the arts. For purposes of discussion, however, the process may implement any of a wide variety of commercially available heat shrink film or tubing. The magnets 106 and 108 are first positioned within the heat shrink tubing. The magnets are readily positioned while the heat shrink tubing is in an initial state (e.g., at room temperature) prior to processing. Optionally, the magnet may be pretreated with a coating, e.g., to reduce the effects of corrosion. Application of heat to the heat shrink film or tubing shrinks the film or tubing around the magnets 106 and 108. Shrinkage of the tubing around the magnet applies the necessary pressure to maintain the magnets 106 and 108 in the desired position within the tubing 102 after the heat shrink film or tubing cools.

Also in exemplary embodiments, the catheter 100 can be constructed to have different flexibilities along the length of tubing 102, particularly in the distal region where the magnets are placed. Typically, the portion 124 (FIG. 1) between the distal end (where the tip electrode is located) and the first magnet 106 is desired to be the most flexible. The portion 122 between the first magnet 106 and the second magnet 108 disposed proximally from the first magnet 106 is desired to have less flexibility. Still additional portions and additional magnets may be provided, with the proximal portions having less and less flexibility.

The flexibility can be determined by material properties and/or thickness. Thus, the unitary tubing 102 can be made to have varying material properties along its length toward the distal end, so that the different portions will have different flexibilities. The shaft can also decrease in thickness toward the distal end. A thinner wall of the tubing 102 results in greater flexibility, while a thicker wall of the tubing 102 results in less flexibility.

Flexibility can change either continuously/gradually or in abrupt steps between the segments. The abrupt steps may be useful in defining the locations of the magnets, especially in the embodiment where the magnets are pushed into the shaft with a lubricant. As the magnets 106 and 108 pass through different flexibility zones defined by abrupt steps, the abrupt change in flexibility provides tactile feedback that the magnets 106 and 108 are passing from one flexibility zone to another.

Figure 5:
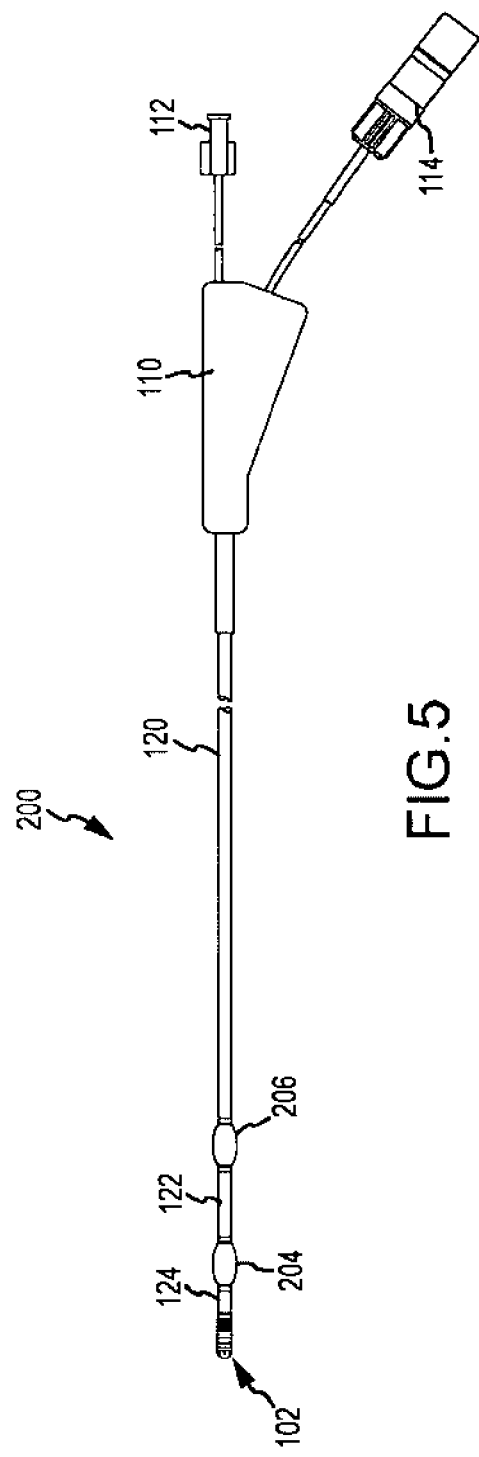
FIG. 5 illustrates a second exemplary embodiment of a magnetic guide catheter.

FIG. 5 illustrates a second exemplary embodiment of a magnetic guided catheter 200 that is similar in many aspects to the catheter 100 described above. Like components and features of the catheter 100 are indicated with like reference characters in FIG. 4. Unlike the catheter 100, the catheter 200 includes magnets 204 and 206 instead of the magnets 106 and 108.

Figure 6:
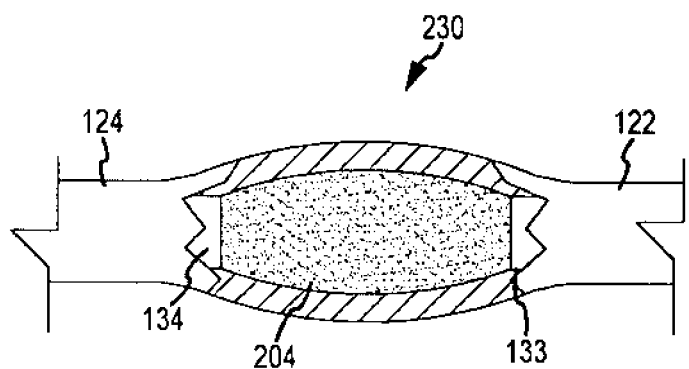
FIG. 6 illustrates a magnet assembly for the catheter shown in FIG. 4.

FIG. 6 illustrates a magnet assembly for the catheter 200. Unlike the magnets 106 and 108 that are cylindrical in shape and have a constant outer diameter, the magnet 204 is outwardly flared and is ellipsoidal in its counter and somewhat resembles a football with truncated ends. That is, the outer diameter of the magnet 204 is largest at the axial midpoint of the magnet, with the outer diameter decreasing from the midpoint to the opposing ends of the magnet 204, providing the magnet 204 with a curved profile along the axial length of the magnet 204.

The magnet 204 is encapsulated in the tube portions 124 and 122 in the manner described above. The tube 133 and the lumen 134 pass centrally through the magnet 204. The magnet may be formed from, for example, neodymium-iron boron-45 (NdFeB-45) into the illustrated shape or an alternative shape. The magnet 206 (FIG. 6) may be formed in the same or different shape from the magnet 204.

Figures 7, 8:
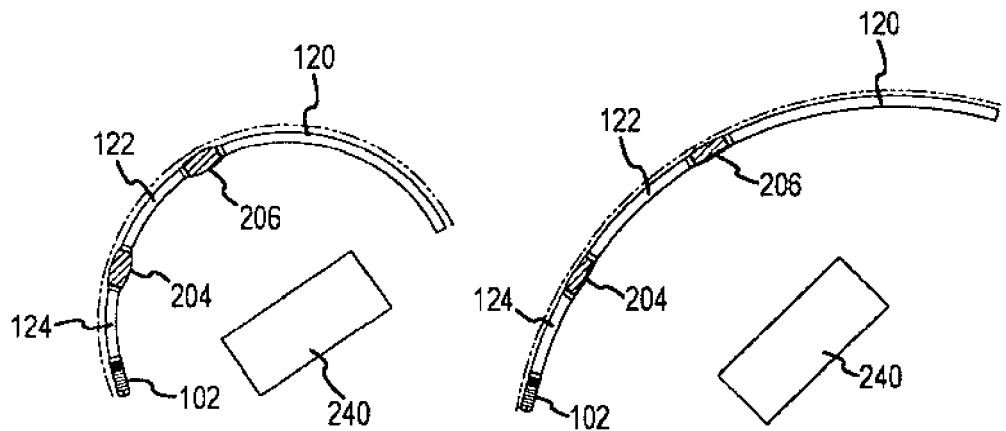
FIG. 7 illustrates the catheter shown in FIG. 4 in a first operating position.
FIG. 8 illustrates the catheter shown in FIG. 4 in a second operating position.

FIG. 7 and FIG. 8 illustrate the catheter 200 in exemplary first and second operating positions with the distal end including the tip assembly 102 deflected to different positions with the magnets 204 and 206. By applying magnetic fields to the magnets 204 and 206, and also the magnet 224 (FIG. 7) in the tip, the distal end of the catheter 200 may be moved to desired positions within a patient's body. The magnetic fields may be generated and controlled by, for example, a magnetic stereotactic system 240. By virtue of the positioning magnet in the tip and the external magnets 204 and 206, the tip may be precisely positioned at a specific location within the patient's body.

The unitary construction of the flexible tubings of the catheters 100 and 200 is believed to provide manufacturing benefits, and also performance benefits, in relation to conventional, and more complicated, catheter constructions for use with stereotactic systems. The catheter can be manufactured without requiring magnet-shaft fusion and without joints, ensuring high reliability and safety of the catheter. The unitary tubing is easier to manufacture, takes less time to manufacture, and does not require an expensive and complicated fusion machine. Eliminating the junction of the magnet and the shall also reduces or altogether eliminates undesirable stiffness. In addition, the magnets that are separately provided from the electrode tips also reduces complexity and parts count in the tip assembly relative to other known catheter tips providing comparable functionality. The unitary flexible tubing may extend along substantially the entire length of the catheter body, and may have a distal end to be coupled to an electrode assembly and a proximal end to be coupled to a handle. Alternatively, the unitary flexible tubing may extend along a portion of the catheter body with no fused connections between the magnets, but may be attached to additional components to form the entire length of the catheter body. For example, the unitary flexible tubing containing the magnets with no fused connections may be fused with another flexible tubing to form the entire length of the catheter body.

While the invention has been described in terms of various specific embodiments, those skilled in the art will recognize that the invention can be practiced with modification within the spirit and scope of the claims.

What is claimed is:

1. A method of manufacturing a catheter comprising:
   providing a unitary flexible tubing having a proximal end and a distal end;
   providing a plurality of magnets; and positioning the plurality of magnets positioned along an axis of the unitary flexible tubing by pushing the plurality of magnets into the unitary flexible tubing and expanding an inner diameter of the unitary flexible tubing to a shape of the plurality of magnets where the magnets are positioned, and wherein the plurality of magnets in the unitary flexible tubing are configured to be responsive to an external magnetic field for selectively positioning and guiding the catheter within a body of a patient; and forming an electrode assembly at the distal end of the unitary flexible tubing that includes providing a distal magnet therewith, and wherein the distal magnet of the electrode assembly is a first magnet, and wherein pushing the plurality of magnets into the unitary flexible tubing comprises pushing second and third magnets of the plurality of magnets into the unitary flexible tubing, and wherein the third magnet is spaced from the second magnet which is spaced from the first magnet along the axis of the unitary flexible tubing, wherein the second magnet is spaced from the first magnet by a first distance along the axis of the unitary flexible tubing, and the third magnet is spaced a second distance from the second magnet along the axis of the tubing, and wherein the second distance is greater than the first distance.

2. The method of claim 1 further comprising lubricating the unitary flexible tubing to facilitate positioning the plurality of magnets therein.

3. The method of claim 1 further comprising lubricating the unitary flexible tubing with alcohol to facilitate positioning the plurality of magnets therein.

4. The method of claim 1 wherein providing the unitary flexible tubing comprises increasing a flexibility of the unitary flexible tubing at a distal portion of the unitary flexible tubing relative to a proximal portion of the unitary flexible tubing.

5. The method of claim 1 wherein providing the unitary flexible tubing comprises providing a plurality of segments of different flexibility along the unitary flexible tubing.

6. The method of claim 5 wherein providing a plurality of segments of different flexibility comprises forming the unitary flexible tubing with a first thickness of tubing walls at a most proximal one of the plurality of segments, and forming the unitary flexible tubing with tubing walls of decreasing thickness in a direction toward a most distal one of the plurality of segments.

7. The method of claim 5 wherein providing a plurality of segments of different flexibility further comprises providing the plurality of segments of the unitary flexible tubing with different material properties to provide increasing flexibility of the segments from a most proximal one of the plurality of segments to a most distal one of the plurality of segments.

8. The method of claim 1 wherein pushing the plurality of magnets into the unitary flexible tubing comprises pushing two magnets into the unitary flexible tubing.

9. The method of claim 1 wherein providing the plurality of magnets comprises providing the plurality of magnets with an outer diameter that is larger than the inner diameter of the unitary flexible tubing, wherein expanding the inner diameter of the unitary flexible tubing to the shape of the plurality of magnets establishes an interference fit.

10. The method of claim 1 wherein providing the plurality of magnets includes providing the plurality of magnets with a cylindrical shape.

11. The method of claim 1 wherein providing the plurality of magnets includes providing the plurality of magnets with an ellipsoid shape.

12. The method of claim 1 further comprising inserting an elongate inner tube defining a central lumen through the unitary flexible tubing and through respective central bores formed in the plurality of magnets.

13. A method of manufacturing a catheter comprising:
providing a unitary flexible tubing having a proximal end and a distal end;
providing a plurality of magnets; and
positioning the plurality of magnets positioned along an axis of the unitary flexible tubing by pushing the plurality of magnets into the unitary flexible tubing and expanding an inner diameter of the unitary flexible tubing to a shape of the plurality of magnets where the magnets are positioned, and wherein the plurality of magnets in the unitary flexible tubing are configured to be responsive to an external magnetic field for selectively positioning and guiding the catheter within a body of a patient, and
wherein pushing the plurality of magnets into the unitary flexible tubing comprises:
mounting a first one of the plurality of magnets on a first mandrel at a first position that is a first distance from a stop surface of the first mandrel;
mounting a second one of the plurality of magnets on a second mandrel at a second position that is a second distance from a stop surface of the second mandrel;
pushing the first mandrel into the unitary flexible tubing until the stop surface of the first mandrel abuts one of the proximal and distal ends of the unitary flexible tubing;
removing the first mandrel from the unitary flexible tubing, leaving the first one of the plurality of magnets positioned in the unitary flexible tubing;
inserting the second mandrel into the unitary flexible tubing until the stop surface of the second mandrel abuts said one end of the unitary flexible tubing;
removing the second mandrel from the unitary flexible tubing, leaving the second one of the plurality of magnets positioned in the unitary flexible tubing.

14. The method claim 13 further comprising selecting the first distance to be greater than the second distance wherein the first and second ones of the plurality of magnets are separated by a separation distance corresponding to the difference between the first distance and the second distance.

15. The method of claim 14 wherein inserting the first mandrel and inserting the second mandrel are performed separately and sequentially.

* * * * *